(12) United States Patent
Xu et al.

(10) Patent No.: US 12,331,014 B2
(45) Date of Patent: Jun. 17, 2025

(54) ALDEHYDE BYPRODUCT REDUCTION IN ACRYLIC ACID PRODUCTION USING HIGHLY ACTIVE AND ELECTIVE CATALYSTS

(71) Applicants: Dow Global Technologies LLC, Midland, MI (US); Rohm and Haas Company, Collegeville, PA (US)

(72) Inventors: Jinsuo Xu, Berwyn, PA (US); Nelson I. Quiros, Houston, TX (US); Daniel A. Bors, Maple Glen, PA (US); Joseph F. Dewilde, King of Prussia, PA (US)

(73) Assignees: Rohm and Haas Company, Collegeville, PA (US); Dow Global Technologies LLC, Midland, MI (US)

( * ) Notice: Subject to any disclaimer, the term of this patent is extended or adjusted under 35 U.S.C. 154(b) by 678 days.

(21) Appl. No.: 17/601,751

(22) PCT Filed: Apr. 20, 2020

(86) PCT No.: PCT/US2020/028907
§ 371 (c)(1),
(2) Date: Oct. 6, 2021

(87) PCT Pub. No.: WO2020/223048
PCT Pub. Date: Nov. 5, 2020

(65) Prior Publication Data
US 2022/0193640 A1    Jun. 23, 2022

Related U.S. Application Data

(60) Provisional application No. 62/841,921, filed on May 2, 2019.

(51) Int. Cl.
*C07C 51/16* (2006.01)
*B01J 23/00* (2006.01)
(Continued)

(52) U.S. Cl.
CPC ............. *C07C 51/16* (2013.01); *B01J 23/002* (2013.01); *B01J 23/28* (2013.01); *B01J 23/6525* (2013.01);
(Continued)

(58) Field of Classification Search
CPC ......... C07C 45/28; C07C 51/16; C07C 57/04; B01J 23/28
See application file for complete search history.

(56) References Cited

U.S. PATENT DOCUMENTS 5,677,261 A * 10/1997 Tenten .................. C07C 51/252
                                                        502/316
5,959,143 A      9/1999 Sugi et al.
(Continued)

FOREIGN PATENT DOCUMENTS

DE    19753817    *  6/1999 ............. C07C 45/33
EP    0792866 B1    6/2000
(Continued)

OTHER PUBLICATIONS

Ishikawa, Catal. Sci. Technol., 2016, 6, 617-629.

*Primary Examiner* — Yate' K Cutliff
(74) *Attorney, Agent, or Firm* — Brian L. Mutschler

(57) ABSTRACT

A catalyst composition comprises an acrolein-oxidizing catalyst comprising a mixed metal oxide catalyst of general formula (1):

$$MoV_aA^1_bA^2_cA^3_dO_m \quad (I)$$

in which $A^1$ comprises at least one element selected from the group consisting of W and Cu; $A^2$ comprises at least one element selected from the group consisting of Sb, Fe, and Nb; $A^3$ comprises at least one element selected from the group consisting of Y, Ti, Zr, Hf, Ta, Cr, Mn, Re, Ru, Co, Rh, Ir, Ni, Pd, Pt, Ag, Au, Zn, B, Al, Ga, In, Ge, Sn, Si, Te, Pb, (Continued)

P, As, Bi, Se, rare earth elements, alkaline elements, and alkaline earth elements; a ranges from 0.01 to 1.0; b ranges from 0.01 to 1.5; c ranges from 0 to 1.5; d ranges from 0 to 1.0; and m is dependent on the oxidation state of the other elements. The catalyst composition further comprises a finishing catalyst comprising a mixed metal oxide catalyst of general formula (II):

$$MoV_wNb_xX^1_yX^2_zO_n \qquad (II)$$

in which $X^1$ comprises at least one element selected from the group consisting of Te and Sb; $X^2$ comprises at least one an element selected from the group consisting of Y, Ti, Zr, Hf, Nb, Ta, Cr, Mn, Re, Fe, Ru, Co, Rh, Ir, Ni, Pd, Pt, Ag, Au, Zn, B, Al, Ga, In, Ge, Sn, Pb, P, As, Bi, Se, rare earth elements and alkaline earth elements; w ranges from 0.01 to 1.0; x ranges from 0.01 to 1.0; y ranges from 0.01 to 1.0; z ranges from 0 to 1.0; and n is depended on the oxidation state of the other elements. The finishing catalyst does not contain W or Cu, and has an X-ray diffraction pattern showing an orthorhombic phase as the major crystal phase with main peaks with 2θ at 6.7°, 7.8°, 22.1°, and 27.2°. The acrolein-oxidizing catalyst has a different chemical composition than the finishing catalyst. A process for producing acrylic acid is also disclosed.

6 Claims, 3 Drawing Sheets (51) Int. Cl.
  B01J 23/28 (2006.01)
  B01J 23/652 (2006.01)
  C07C 45/28 (2006.01)
  C07C 57/04 (2006.01)
(52) U.S. Cl.
  CPC .............. C07C 45/28 (2013.01); C07C 57/04 (2013.01); *B01J 2523/55* (2013.01); *B01J 2523/56* (2013.01); *B01J 2523/64* (2013.01)

(56) References Cited

U.S. PATENT DOCUMENTS

| | | | |
|---|---|---|---|
| 6,383,978 | B1 | 5/2002 | Bogan, Jr. et al. |
| 6,388,129 | B1* | 5/2002 | Machhammer ....... C07C 51/252 562/545 |
| 6,403,525 | B1 | 6/2002 | Chaturvedi et al. |
| 6,407,031 | B1 | 6/2002 | Chaturvedi et al. |
| 6,407,280 | B1 | 6/2002 | Chaturvedi et al. |
| 6,518,216 | B1 | 2/2003 | Han et al. |
| 6,589,907 | B2 | 7/2003 | Chaturvedi et al. |
| 6,641,996 | B1 | 11/2003 | Jefferson et al. |
| 6,812,366 | B2 | 11/2004 | Lin et al. |
| 7,048,834 | B2 | 5/2006 | Ishii et al. |
| 7,217,680 | B2 | 5/2007 | Teshigahara et al. |
| 7,304,014 | B2 | 12/2007 | Cavalcanti et al. |
| 7,365,228 | B2 | 4/2008 | Shin et al. |
| 7,875,571 | B2 | 1/2011 | Bogan, Jr. et al. |
| 8,623,780 | B2 | 1/2014 | Li et al. |
| 9,181,169 | B2 | 11/2015 | Welker-Nieuwoudt et al. |
| 9,616,415 | B2 | 4/2017 | Xu et al. |
| 2003/0004379 | A1 | 1/2003 | Gaffney et al. |
| 2005/0272952 | A1* | 12/2005 | Cremer ................. C07C 51/252 562/545 |
| 2005/0277546 | A1 | 12/2005 | Hibst et al. |
| 2007/0167650 | A1 | 7/2007 | Ishikawa et al. |
| 2009/0076303 | A1* | 3/2009 | Han ........................ C07C 51/36 562/606 |
| 2013/0281737 | A1 | 10/2013 | Charendorff et al. |

FOREIGN PATENT DOCUMENTS

| | | |
|---|---|---|
| EP | 1192988 | 4/2002 |
| EP | 1249274 | 10/2002 |
| EP | 1080784 B1 | 4/2005 |
| EP | 1270068 B1 | 4/2006 |
| EP | 1192984 B1 | 7/2006 |
| EP | 1192982 B1 | 8/2006 |
| EP | 1192987 B1 | 8/2006 |
| EP | 1192983 B1 | 11/2006 |
| EP | 1749573 | 2/2007 |
| EP | 1192986 B1 | 8/2007 |
| WO | 2005120702 | 12/2005 |

\* cited by examiner

ALDEHYDE BYPRODUCT REDUCTION IN ACRYLIC ACID PRODUCTION USING HIGHLY ACTIVE AND ELECTIVE CATALYSTS

FIELD OF THE INVENTION

The present invention relates to catalysts and processes for producing acrylic acid and, more particularly, to highly active and selective catalysts and processes using such catalysts for reducing aldehyde byproducts in acrylic acid production.

BACKGROUND OF THE INVENTION

Acrylic acid and its esters are industrially important for manufacturing polymers for a very wide range of application including, but not limited to, adhesives, coatings, films, biomedical carriers and devices, and binders. Acrylic acid may be produced, among other methods, by catalytic gas-phase oxidation of alkanes, alkanols, alkenes, or alkenals.

One widely practiced process is, for example, catalytic gas-phase oxidation of propane, propene, or acrolein. These starting materials are generally diluted with inert gases such as nitrogen, carbon monoxide, carbon dioxide, saturated hydrocarbons and/or steam, and then contacted with a mixed metal oxide catalyst (e.g., a mixed metal oxide catalyst containing one or more of molybdenum (Mo), vanadium (V), tungsten (W), and iron (Fe)), with or without molecular oxygen, at elevated temperatures (e.g., from 20° C. to 400° C.) to be oxidized into acrylic acid.

Mixed metal oxide catalyst containing Mo and V as main elements have been used in the oxidation of acrolein to acrylic acid. The oxidation of acrolein to acrylic acid, for example, is the second step when using propylene to make acrylic acid. The mixed metal oxide catalyst generally contains one or more elements selected from W, copper (Cu), and nickel (Ni), in addition to Mo and V, and are very selective in oxidizing acrolein to acrylic acid with yield generally 92% and above. However, due to the high temperature and formation of "hot spots" (i.e., locations within the catalyst bed where the temperature is higher than the bath temperature) from such an exothermic reaction, the activity and selectivity of the mixed oxide catalyst deteriorate over time, leading to decreased acrylic acid yield and frequent catalyst replacement.

Improvements have been made to reduce the catalyst deactivation and extend the lifetime of the catalyst. For example, European Patent No. EP 0792866 reported the use of different size catalyst pellets such that the particle size becomes smaller from the raw material gas inlet side to the outlet side to reduce the reactor temperature and hot spots, thus extending the catalyst lifetime.

European Patent Application Publication No. EP 1749573A1 discloses the use of at least two reactions zones with different activity through changing the catalyst composition to reduce the rate of temperature increase over time in order to extend the catalyst lifetime. The catalysts contain Mo, V, antimony (Sb), Cu, and at least one of niobium (Nb) and W, and may also contain silicon (Si) and carbon (C).

U.S. Pat. No. 7,365,228 discloses the use of an inactive material layer next to the catalyst layer that generates "hot spots" to reduce the peak temperature among the hot spots in order to increase the lifetime of the catalyst and achieve higher yield of acrylic acid.

U.S. Pat. No. 8,623,780 discloses the use of organic reducing agent including C2-C6 diol or polyol and silicon powder during preparation process of the mixed metal oxide and/or molding process of the catalyst to boost activity of the catalyst and increase heat transfer efficiency along the catalyst bed. As a result, the 'hot spots" are reduced and the catalyst lifetime and acrylic acid yield can be increased.

U.S. Pat. No. 9,181,169 discloses hydrothermal synthesis of the mixed metal oxide to increase its activity and yield towards acrylic acid.

Overall, these efforts are effective in boosting the lifetime of the mixed oxide catalyst. However, other issues exist when using those catalysts and methods.

Since there are numerous parallel and subsequent reactions occurring in the course of the catalytic vapor phase oxidation, and because of the inert diluent gases used, the resulting mixed gas product contains not only acrylic acid, but also inert diluent gases, impurities, and byproducts, from which the acrylic acid has to be separated. Thus, the mixed product gas is next typically subjected to absorption to remove acrylic acid from some of the byproducts and impurities and form an acrylic acid solution. It is known to use an absorption solvent such as water or a hydrophobic organic liquid (e.g., without limitation, toluene, methyl isobutyl ketone (MiBK, and diphenyl ether) or the acrylic acid itself (e.g., as in a fractionating column) for the absorption step. The resulting acrylic acid solution is then subjected to further separation and purification steps, such as by azeotropic or simple distillation, or crystallization, or extraction, to produce a crude acrylic acid product, which may or may not be subjected to further purification or reaction as desired, depending on the intended end-use.

Besides byproducts which are comparatively simple to remove from acrylic acid, such as acetic acid, the mixed gas product also contains aldehyde compounds, which are closely related to acrylic acid in terms of boiling point and/or solubility and, therefore, can be difficult to separate from acrylic acid. The aldehydes byproducts form in the oxidation product may include, for example, one or more of the following: formaldehyde, acetaldehyde, acrolein, propionaldehyde, benzaldehyde, phthaldehyde, furfural, protoanemonin, and possibly also maleic anhydride or its acid. The total amount of aldehyde components present in the mixed gas product may be up to, or even more than, about 2 wt. % based on the total weight of the mixed gas product obtained from the oxidation reaction. Aldehyde compounds, especially the lower molecular $C_1$ to $C_3$ analogues (formaldehyde, acetaldehyde, and propionaldehyde), have been reported to initiate polymerization of acrylic acid in separations equipment such as distillation columns, reboilers, and heat exchanger equipment. In particular, formaldehyde has been shown in the art as contributing to solids when placed in contact with common polymerization inhibitors such as phenothiazine (PTZ), hydroquinone (HQ), and hydroquinone monomethyl ether (MeHQ) (see, e.g., U.S. Patent Application Publication No. 2007/0167650). Furfural and acrolein have also been reported as fouling contributors in the processing of acrylic acid.

For the production of glacial acrylic acid (GAA) or flocculant glacial acrylic acid (FGAA), it is necessary to reduce the amount of certain aldehydes, such as, for example, acrolein, furfural, and benzaldehyde, below 1 ppm.

Attempts have been made to reduce the amount of aldehydes formed during the production of acrylic acid. These methods reduce aldehyde impurities in crude acrylic acid using chemical scavengers selected from primary and secondary amines or their salts, such as hydrazides or m-phenylenediamine (m-PD), to react with aldehydes and form adducts with higher boiling points. The high boiling point adducts are left in the distillation column bottoms stream while purer acrylic acid is obtained as the distillate. Such methods are disclosed, for example, in U.S. Pat. No. 7,048,834 and U.S. Patent Application Publication No. 2013/0281737.

These methods, however, require excess amounts of the chemical scavengers to reduce the aldehyde concentration to desired levels, which add extra cost to the production of acrylic acid, in addition to increasing dimer formation. Increased fouling from these chemical scavengers has also been observed in downstream processes such as distillation or esterification.

Additionally, the chemical scavengers can also cause other issues besides increased cost and/or fouling. For example, m-PD is difficult to handle because it is a solid at ambient condition and can be oxidized easily to compound with color.

A new class of mixed metal oxide catalysts containing the elements Mo, V, Nb, and tellurium (Te) or Sb have been found to be active and selective to oxidize propane to acrylic acid. For example, U.S. Pat. Nos. 7,875,571; 7,304,014; and 9,616,415 disclose compositions and preparation methods of MoVTeNb oxide catalysts for direct propane oxidation to acrylic acid. U.S. Patent Application Publication No. 2009/0076303 reported using MoVTeNb oxide catalyst for reducing propionic acid, an impurity in acrylic acid from direct propane oxidation. While MoVTeNb oxide could be used for acrolein oxidation to acrylic acid, as reported in U.S. Pat. No. 6,812,366, the yield (89.4%, Example 7) was lower than 92%+ yield reported when using MoV-based mixed metal oxide catalysts optimized for selective acrolein oxidation to acrylic acid.

Therefore, there is a need for catalysts and methods of producing acrylic acid in high yield that can reduce the temperature and/or amount of aldehydes.

SUMMARY OF THE INVENTION

One aspect of the present invention relates to a catalyst composition comprising:
a) an acrolein-oxidizing catalyst comprising a mixed metal oxide catalyst of general formula (I):

$$MoV_aA^1_bA^2_cA^3_dO_m \qquad (I)$$

wherein:
A$^1$ comprises at least one element selected from the group consisting of W and Cu;
A$^2$ comprises at least one element selected from the group consisting of Sb, Fe, and Nb;
A$^3$ comprises at least one element selected from the group consisting of Y, Ti, Zr, Hf, Ta, Cr, Mn, Re, Ru, Co, Rh, Ir, Ni, Pd, Pt, Ag, Au, Zn, B, Al, Ga, In, Ge, Sn, Si, Te, Pb, P, As, Bi, Se, rare earth elements, alkaline elements, and alkaline earth elements;
a ranges from 0.01 to 1.0;
b ranges from 0.01 to 1.5;
c ranges from 0 to 1.5;
d ranges from 0 to 1.0;
m is dependent on the oxidation state of the other elements;
b) a finishing catalyst comprising a mixed metal oxide catalyst of general formula (II):

$$MoV_wNb_xX^1_yX^2_zO_n \qquad (II)$$

wherein:
X$^1$ comprises at least one element selected from the group consisting of Te and Sb;
X$^2$ comprises at least one an element selected from the group consisting of Y, Ti, Zr, Hf, Nb, Ta, Cr, Mn, Re, Fe, Ru, Co, Rh, Ir, Ni, Pd, Pt, Ag, Au, Zn, B, Al, Ga, In, Ge, Sn, Pb, P, As, Bi, Se, rare earth elements and alkaline earth elements;
w ranges from 0.01 to 1.0;
x ranges from 0.01 to 1.0;
y ranges from 0.01 to 1.0;
z ranges from 0 to 1.0;
n is depended on the oxidation state of the other elements;
the finishing catalyst does not contain W or Cu, and has an X-ray diffraction pattern showing an orthorhombic phase as the major crystal phase with main peaks with 2θ at 6.7°, 7.8°, 22.1°, and 27.2°; and
the acrolein-oxidizing catalyst has a different chemical composition than the finishing catalyst.

A second aspect of the present invention relates to a process for producing acrylic acid comprising:
a) contacting a gas stream comprising acrolein with an acrolein-oxidizing catalyst to form a product stream A, wherein at least one aldehyde byproduct is present in the product stream A;
b) contacting the product stream A with a finishing catalyst to form a product stream B comprising acrylic acid, wherein the product stream B comprises a lower weight percentage of the at least one aldehyde byproduct than product stream A;
wherein:
i) the acrolein-oxidizing catalyst comprises a mixed metal oxide catalyst of general formula (I):

$$MoV_aA^1_bA^2_cA^3_dO_m \qquad (I)$$

wherein:
A$^1$ comprises at least one element selected from the group consisting of W and Cu;
A$^2$ comprises at least one element selected from the group consisting of Sb, Fe, and Nb;
A$^3$ comprises at least one element selected from the group consisting of Y, Ti, Zr, Hf, Ta, Cr, Mn, Re, Ru, Co, Rh, Ir, Ni, Pd, Pt, Ag, Au, Zn, B, Al, Ga, In, Ge, Sn, Si, Te, Pb, P, As, Bi, Se, rare earth elements, alkaline elements, and alkaline earth elements;
a ranges from 0.01 to 1.0;
b ranges from 0.01 to 1.5;
c ranges from 0 to 1.5;
d ranges from 0 to 1.0; and
m is dependent on the oxidation state of the other elements;
ii) the finishing catalyst comprising a mixed metal oxide catalyst of general formula (I):

$$MoV_wNb_xX^1_yX^2_zO_n \qquad (II)$$

wherein:
X$^1$ comprises at least one element selected from the group consisting of Te and Sb;
X$^2$ comprises at least one an element selected from the group consisting of Y, Ti, Zr, Hf, Nb, Ta, Cr, Mn, Re, Fe, Ru, Co, Rh, Ir, Ni, Pd, Pt, Ag, Au, Zn, B, Al, Ga, In, Ge, Sn, Pb, P, As, Bi, Se, rare earth elements and alkaline earth elements;
w ranges from 0.01 to 10;
x ranges from 0.01 to 1.0;
y ranges from 0.01 to 1.0;
z ranges from 0 to 1.0;
n is depended on the oxidation state of the other elements;

the finishing catalyst does not contain W or Cu, and has an X-ray diffraction pattern showing an orthorhombic phase as the major crystal phase with main peaks with 2θ at 6.7°, 7.8°, 22.1°, and 27.2°; and the acrolein-oxidizing catalyst has a different chemical composition than the finishing catalyst.

DETAILED DESCRIPTION OF EMBODIMENTS OF THE INVENTION

As used herein, the terms "a," "an," "the," "at least one," "one or more," and variations thereof are used interchangeably. The terms "comprises," "includes," "contains," and variations thereof do not have a limiting meaning where these terms appear in the description and claims. Thus, for example, a first mixed metal oxide catalyst composition that includes a polymerization inhibitor can be interpreted to mean that the composition comprises at least one polymerization inhibitor.

As used herein, recitations of numerical ranges by endpoints includes all numbers subsumed in that rage (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.1 to 100, from 1 to 99.99, from 1.01 to 99.99, from 40 to 6, from 1 to 55, etc.

As used herein, the recitations of numerical ranges and/or numerical values, including such recitations in the claims, can be read to include the term "about." In such instances, the term "about" refers to numerical ranges and/or numerical values that are substantially the same as those recited herein. When multiple endpoints are disclosed, it is intended that the disclosure covers any range between any two disclosed endpoints.

As used herein, mixed metal oxide catalyst refers to a catalyst comprising more than one metal oxide. Such mixed metal oxide catalysts may be formed on a support, such as, for example, silica, alumina, silica carbide, or other material known in the art that does not alter the catalytic activity. The chemical formulae disclosed herein are directed to the active catalyst material and exclude any support. For example, in general formula (I), below, $A^3$ may comprise silicon. In general formula (I), d includes only the amount of silicon, if present, in the active catalyst material, and excludes any silicon in the support material.

Unless stated to the contrary, or implicit from the context, all parts and percentages are based on weight and all test methods are current as of the filing date of this application. For purposes of United States patent practice, the contents of any referenced patent, patent application or publication are incorporated by referenced in their entirety or its equivalent U.S. version is so incorporated by reference) especially with respect to the disclosure of definitions (to the extent not inconsistent with any definitions specifically provided in this disclosure) and general knowledge in the art.

The inventors have surprisingly discovered that a finishing catalyst comprising a mixed metal oxide containing M, V, Nb, and at least one element selected from Te and Sb may reduce the temperature required, which may in turn slow down the deactivation of the catalysts used in the production of acrylic acid and extend the lifetime of the catalyst. Surprisingly, the finishing catalyst may also reduce the amounts of aldehyde byproducts in the product stream and may increase the acrylic acid yield compared to the use of conventional catalysts alone. The reduction of aldehyde byproducts in the product stream may reduce the use of chemical scavengers and may alleviate the fouling in downstream processes.

One aspect of the present invention relates to a catalyst composition comprising two mixed metal oxide catalyst. A first catalyst is an acrolein-oxidizing catalyst, i.e., the primary function of the acrolein-oxidizing catalyst is the gas-phase oxidation of acrolein to produce acrylic acid. The second catalyst is a mixed metal oxide finishing catalyst. The finishing catalyst enables the catalyst composition to solve one or more of the problems of conventional mixed metal oxide catalysts used to produce acrylic acid, while maintaining a high yield of acrylic acid.

The acrolein-oxidizing catalyst has a different chemical composition than the finishing catalyst. As used herein, the term "different chemical composition" means the catalyst compositions have a different molecular formula. For example, the catalyst compositions may differ in the elements they contain, or the catalyst compositions may differ in the ratio of elements they contain. Preferably, the acrolein-oxidizing catalyst differs from the finishing catalyst in the elements contained.

The finishing catalyst is preferably more active in the range of 200 to 350° C. towards aldehyde oxidation than the acrolein-oxidizing catalyst.

The acrolein-oxidizing catalyst may comprise Mo and V as the main elements. Preferably, the acrolein-oxidizing catalyst is a mixed metal oxide catalyst of general formula (I):

$$MoV_aA^1_bA^2_cA^3_dO_m \quad (I)$$

The mixed metal oxide catalyst of general formula (I) comprises at least three metal oxides, including Mo oxide and V oxide, i.e., a and b are greater than zero. Preferably, a is at least 0.01, such as, for example, at least 0.05, at least 0.1, at least 0.2, at least 0.3, at least 0.4, or at least 0.5. In general formula (I), a is less than or equal to 1.0, such as, for example, less than 0.9, less than 0.8, or less than 0.7. Preferably, a ranges from 0.1 to 0.6.

In general formula (I), $A^1$ may comprise at least one element selected from W and Cu. When $A^1$ comprises more than one element, the amount of each element may be the same or different. $A^1$ is a necessary element in general formula (I). Therefore, the amount of $A^1$ in general formula (I), b, is greater than zero. For example, b may be at least 0.01, at least 0.03, at least 0.05, at least 0.1, at least 0.15, or at least 0.2. In general formula (I), b may be less than or equal to 1.5, such as, for example, less than 1.0, less than 0.8, less than 0.6, or less than 0.5. Preferably, b ranges from 0.2 to 0.3.

$A^2$ may comprise Sb, Fe, or Nb, or combinations of two or three of these elements. $A^2$ is an optional component of general formula (I), i.e., c is equal to zero. Alternatively, c may be greater than zero, such as at least 0.01, at least 0.02, or at least 0.05. In general formula (I), c is less than 1.5, preferably, less than 1.0, less than 0.5, less than 0.4, less than 0.3, or less than 0.2. Preferably, c ranges from 0.05 to 0.2.

In general formula (I), $A^3$ may comprises at least one element selected from Y, Ti, Zr, Hf, Ta, Cr, Mn, Re, Ru, Co, Rh, Ir, Ni, Pd, Pt, Ag, Au, Zn, B, Al, Ga, In, Ge, Sn, Si, Te, Pb, P, As, Bi, Se, rare earth elements, alkaline elements, and alkaline earth elements. $A^3$ is an optional element in general formula (I), i.e., d may equal zero. Alternatively, d may be greater than zero. If present, $A^3$ is preferably selected from alkaline or alkaline earth elements.

In general formula (I), d is less than or equal to 1.0. Preferably, d is less than or equal to 0.8, less than or equal to 0.6, less than or equal to 0.5, less than or equal to 0.4, less than or equal to 0.3, or less than or equal to 0.25. d may be greater than or equal to 0, such as, for example, greater than or equal to 0.05, greater than or equal to 0.1, or greater than or equal to 0.2. Preferably, d ranges from 0.05 to 0.25

In general formula (I), m is dependent on the oxidation state of the other elements.

The preparation of mixed metal oxide catalysts that may be included within general formula (I) is described, for example U.S. Pat. Nos. 5,959,143, 6,383,978; 6,641,996; 6,518,216; 6,403,525; 6,407,031; 6,407,280; and 6,589,907; U.S. Publication Application No. 20030004379; U.S. Provisional Application Ser. Nos. 60/235,977; 60/235,979; 60/235,981; 60/235,984; 60/235,983; 60/236,000; 60/236,073; 60/236,129; 60/236,143; 60/236,605; 60/236,250; 60/236,260; 60/236,262; 60/236,263; 60/283,245; and 60/286,218; and EP Patent Nos. EP 1 080784; EP 1 192 982; EP 1 192 983; EP 1 192 984; EP 1 192 986; EP 1 192 987; EP 1 192 988; EP 1 192 982; EP 1 249 274; and EP 1 270 068. The synthesis of such mixed metal oxide catalysts can be accomplished by any of several methods well known by those having skill in the art.

The acrolein-oxidizing catalyst is preferably highly selective in oxidizing acrolein to acrylic acid with a yield of at least 90%, such as, for example, a yield of at least 91%, at least 92%, at least 93%, or at least 94%.

The finishing catalyst may comprise a mixed metal oxide catalyst of general formula (II):

$$MoV_wNb_xX^1_yX^2_zO_n \qquad (II)$$

In general formula (II), $X^1$ comprises at least one element selected from Te, Sb, and combinations of Te and Sb.

For the mixed metal oxides of general formula (II), each of w, x, and y are greater than zero. Therefore, the mixed metal oxide catalysts of general formula (II) comprise MoVNbTe-based oxides and MoVNbSb-based oxides. Preferably, the mixed metal oxide catalysts of general formula (II) consist of MoVNbTe oxides or MoVNbSb oxides, i.e., z is 0.

The finishing catalyst of general formula (II) comprises V in an amount w ranging from 0.01 to 1.0, inclusive. Preferably, w is at least 0.1, such as, for example, at least 0.2, at least 0.3, or at least 0.4. w is less than or equal to 1.0, such as, for example, less than or equal to 0.8, less than or equal to 0.6, or less than or equal to 0.5. Preferably, w ranges from 0.2 to 0.4.

In general formula (II), the amount, x, of Nb in the mixed metal oxide catalyst ranges from 0.01 to 1.0, inclusive. Preferably, x is at least 0.05, such as, for example, at least 0.1, at least 0.15, or at least 0.2. Preferably x is less than or equal to 0.8, less than or equal to 0.6, less than or equal to 0.5, less than or equal to 0.4, or less than or equal to 0.3. Preferably, x ranges from 0.1 to 0.3.

$X^1$, which may be selected from Sb, Te, and combinations of Sb and Te, may be present in an amount, y, ranging from 0.01 to 1.0. Preferably, y is at least 0.02, such as, for example, at least 0.03, at least 0.04, at least 0.05, at least 0.06, at least 0.07, at least 0.08, at least 0.09, or at least 0.1. Preferably, y is less than or equal to 0.5, such as, for example, less than or equal to 0.4, or less than or equal to 0.3. More preferably, y ranges from 0.1 to 0.3.

$X^2$ may comprise at least one element selected from Y, Ti, Zr, Hf, Nb, Ta, Cr, Mn, Re, Fe, Ru, Co, Rh, Ir, Ni, Pd, Pt, Ag, Au, Zn, B, Al, Ga, In, Ge, Sn, Pb, P, As, Bi, Se, rare earth elements, alkaline elements, and alkaline earth elements. Preferably, $X^2$ comprises Pd.

In the mixed metal oxide catalysts of general formula (II), $X^2$ is an optional component, i.e., z may be equal to zero. Alternatively, z may be greater than zero. Preferably, z ranges from 0.001 to 1.0. Preferably, z is greater than or equal to 0.001, such as, for example, greater than or equal to 0.002, greater than or equal to 0.003, greater than or equal to 0.004, or greater than or equal to 0.005. z is preferably less than or equal to 0.5, less than or equal to 0.4, less than or equal to 0.3, less than or equal to 0.2, or less than or equal to 0.1. More preferably, z ranges from 0.005 to 0.1.

The finishing catalyst of general formula (II) does not contain W or Cu.

Preferably, the finishing catalyst of general formula (II) has an X-ray diffraction pattern showing an orthorhombic phase as the major crystal phase with main peaks with 2θ at 6.7°, 7.8°, 22.1°, and 27.2°. As used herein, the term "main peaks" means that the peak intensities are distinctly observed in the X-ray diffraction pattern, i.e., have a signal intensity of at least 1% of the peak with the highest intensity.

The catalyst composition may comprise a layer of the acrolein-oxidizing catalyst and a layer of the finishing catalyst. The layer of the finishing catalyst may be adjacent to the layer of the acrolein-oxidizing catalyst or the layer of the finishing catalyst may be separate from the layer of the acrolein-oxidizing catalyst.

Alternatively, the catalyst composition may have a gradient profile of the catalysts. For example, one end of the catalyst composition may be composed primarily of the acrolein-oxidizing catalyst and the other end may be composed primarily of the finishing catalyst, and the ratio of the two catalysts may vary from one end to the other.

The weight percentage of the finishing catalyst in the catalyst composition may be less than the weight of the acrolein-oxidizing catalyst, e.g., the finishing catalyst comprises less than 50 wt. % of the total weight of the acrolein-oxidizing catalyst and the finishing catalyst. Preferably, the weight of the finishing composition comprises less than 40 wt. %, less than 30 wt. %, less than 25 wt. %, less than 20 wt. %, less than 15 wt. %, or less than 10 wt. % of the total weight of the acrolein-oxidizing catalyst and the finishing catalyst.

The finishing catalyst comprises at least 5 wt. % of the total weight of the acrolein-oxidizing catalyst and the finishing catalyst. Preferably, the finishing catalyst comprises at least 10 wt. %, at least 15 wt. %, or at least 20 wt. % of the total weight of the acrolein-oxidizing catalyst and the finishing catalyst.

Another aspect of the present invention relates to a process for producing acrylic acid.

The process for producing acrylic acid comprises contacting a gas stream comprising acrolein with an acrolein-oxidizing catalyst to form a product stream A. The product stream A comprises acrylic acid and at least one aldehyde byproduct. The at least one aldehyde byproduct in product stream A may include, for example, acetaldehyde, benzaldehyde, or furfural. As used herein, the term "aldehyde byproduct" means an aldehyde formed during the acrylic acid production process. Acrolein, which is an aldehyde, is not an aldehyde byproduct.

Product stream A is then brought into contact with a finishing catalyst to form a product stream B, which comprises acrylic acid. Product stream B comprises a lower weight percentage of the at least one aldehyde byproduct present in product stream A. Product stream B may comprise at least 25% less of the at least one aldehyde byproduct than product stream A, preferably, at least 30% less of the at least one aldehyde byproduct, at least 40% less of the at least one aldehyde byproduct, at least 50% less of the at least one aldehyde byproduct, at least 60% less of the at least one aldehyde byproduct, or at least 70% less of the at least one aldehyde byproduct than product stream A.

Product stream B comprises at least 50% less acetaldehyde than product stream A. Preferably, product stream B comprises at least 60% less acetaldehyde than product stream A, such as, for example, at least 70% less, at least 80% less, or at least 90% less.

The acrolein-oxidizing catalyst and the finishing catalyst used in the present invention may be selected from embodiments of the catalysts disclosed herein. Preferably, the acrolein-oxidizing catalyst is a mixed metal oxide catalyst according to general formula (I) and the finishing catalyst is a mixed metal oxide catalyst according to general formula (II).

The weight ratio of the acrolein-oxidizing catalyst to the finishing catalyst is at least 1:1. The weight ratio of the acrolein-oxidizing catalyst to the finishing catalyst may be at least 2:1, such as, for example, at least 3:1, at least 4:1, at least 5:1, at least 6:1, at least 7:1, at least 8:1, or at least 9:1. Preferably, the weight ratio of the acrolein-oxidizing catalyst to the finishing catalyst is no greater than 20:1, such as, for example, no greater than 16:1, no greater than 14:1, no greater than 12:1, or no greater than 10:1.

The gas stream comprising acrolein may be produced, for example, by oxidizing a feed gas stream comprising an alkane, alkanol, alkene, or alkenal to form acrolein. Preferably, the feed gas stream comprises propane or propylene. More preferably, the feed gas stream comprises propylene. The feed gas stream may be brought into contact with an appropriate oxidizing catalyst known in the art. For example, a suitable propylene-oxidizing catalyst may be selected from commercially available mixed metal oxide catalysts such as Mo- and Bi-based mixed metal oxide catalyst.

Figure 4:
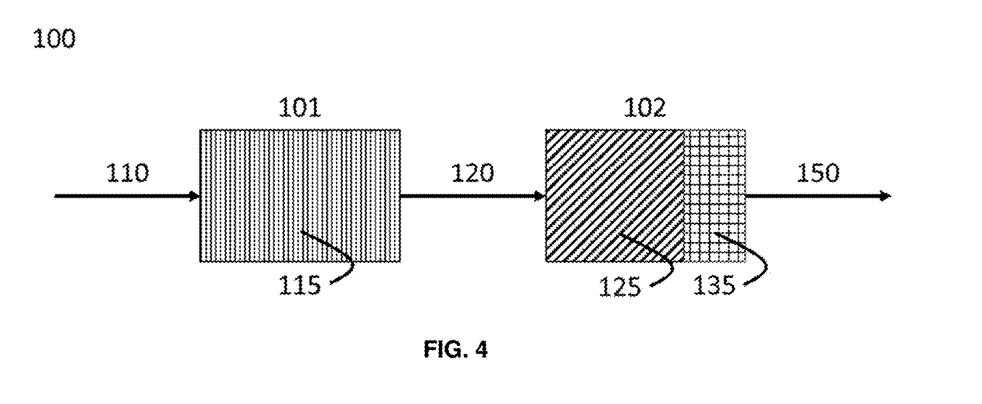
FIG. 4 is a schematic representation of a two-stage reactor process according to an embodiment of the present invention.

The process may be carried out in a two-stage reactor system. A schematic diagram of this embodiment is shown in FIG. 4. In FIG. 4, two-stage reactor system 100 comprises a first stage reactor 101 and a second stage reactor 102.

First stage reactor 101 contains a propylene-oxidizing mixed metal oxide catalyst 115. Second stage reactor 102 contains an acrolein-oxidizing mixed metal oxide catalyst 125 and a finishing catalyst 135.

A gaseous feed stream 110 containing propylene enters the first stage reactor 101 where the propylene comes into contact with a propylene-oxidizing mixed metal oxide catalyst to form a first product stream 120 comprising acrolein.

First product stream 120 enters the second stage reactor 102. The acrolein-oxidizing catalyst 125 and the finishing catalyst 135 are arranged in the second stage reactor 102 such that the first product stream 120 comes into contact with the acrolein-oxidizing catalyst 125 before the gas stream comes into contact with the finishing catalyst 135. Within the second stage reactor 102, the product formed when the first product stream 120 contacts the acrolein-oxidizing catalyst is equivalent to product stream A, described with regard to various embodiments above. Exiting the second stage reactor 102 is a product stream 150 comprising acrylic acid. Product stream 150, which contains the gaseous products of the product stream 120 that have come into contact with both the acrolein-oxidizing catalyst 125 and the finishing catalyst 135, is equivalent to product stream B, discussed in various embodiments above.

Figure 5:
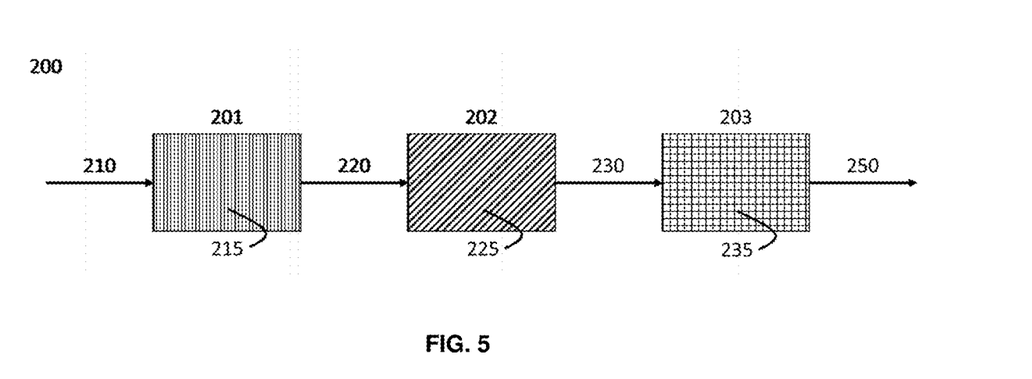
FIG. 5 is a schematic representation of a three-stage reactor process according to an embodiment of the present invention.

Alternatively, the process may be carried out in a three-stage reactor system, such as the one shown schematically in FIG. 5.

In FIG. 5, three-stage reactor system 200 comprises a first stage reactor 201, a second stage reactor 202, and a third stage reactor 203.

First stage reactor 201 contains a propylene-oxidizing mixed metal oxide catalyst 215, second stage reactor 202 contains an acrolein-oxidizing mixed metal oxide catalyst 225, and third stage reactor 203 contains a finishing catalyst 235.

A gaseous feed stream 210 containing propylene enters the first stage reactor 201 where the propylene comes into contact with a propylene-oxidizing mixed metal oxide catalyst to form a first product stream 220 comprising acrolein.

First product stream 220 enters the second stage reactor 202. First product stream 220 contacts acrolein-oxidizing catalyst 225 to selectively oxidize the acrolein to acrylic acid. Second product stream 220 exits the second stage reactor 202 and then enters third stage reactor 203, where the second product stream 220 comes into contact with the finishing catalyst 235 to produce product stream 250.

In the process shown in FIG. 5, product stream 230 is equivalent to product stream A described in certain embodiments above, and product stream 250 is equivalent to product stream B. Product stream 250 contains a lower amount of aldehyde byproducts than product stream 230.

The following examples illustrate the present invention but are not intended to limit the scope of the invention.

EXAMPLES

Synthesis 1 Preparation of Crystalline MoVTeNb Oxide Finishing Catalyst

A finishing catalyst comprising a mixed metal oxide catalyst of nominal composition $Mo_{1.0}V_{0.285}Te_{0.21}Nb_{0.164}Pd_{0.01}O_n$ was produced in the following manner:

An aqueous solution containing Mo(VI), V(V), and Te(IV) salts was formed by dissolving ammonium heptamolybdate tetrahydrate (35.7 g, from Fisher Scientific), ammonium metavanadate (6.74 g, from Sigma Aldrich) and telluric acid (9.74 g, from Sigma Aldrich) sequentially in 200 ml of deionized (D.I.) water that was pre-heated to 70° C. The mixed salt solution was stirred for 20 minutes at 70° C. to ensure that a clear solution was formed. Then, 5 ml of concentrated nitric acid (70 wt. % in water, from Sigma Aldrich) was added to the solution under stirring. Separately, an aqueous solution containing ammonium niobium oxalate (15.24 g, from H. C. Stark, Goslar, Germany) and oxalic acid dihydrate (3.95 g, from Sigma Aldrich) in 180 ml D.I. water was prepared at room temperature.

The Mo/V/Te solution was held under stirring with heating. Then, the heating was stopped and the Nb-containing solution was added to the Mo/V/Te solution. Gelation occurred immediately after the two solutions were mixed. The mixture was stirred for 5 minutes and became a slurry before being transferred to a round-bottom rotary flask.

The water in the slurry was removed via a rotary evaporator at 50° C. under a vacuum of 10-50 mmHg (1.33-6.67 kPa). The solid material was further dried in a vacuum oven overnight at room temperature.

The dried solid material was placed in the middle of a quartz tube with quartz wool stuffed into the tube at both ends of the solid material bed. The tube was placed in the center of an electrical furnace. The material was calcined from room temperature to 275° C. at 10° C./min heating rate in flowing air (80-100 standard cubic centimeters per minute, hereafter SCCM) and holding the temperature at 275° C. for an hour. The flowing gas was then switched to inert gas, such as argon or nitrogen (80-100 SCCM). The furnace temperature was raised to 600° C. from 275° C. at 2° C./min rate and held at 600° C. in an inert gas atmosphere for two hours. This resulted in a MoVTeNb oxide with nominal composition $Mo_{1.0}V_{0.285}Te_{0.21}Nb_{0.164}Pd_{0.01}O_n$.

The crystallinity and crystal phase of the MoVTeNb oxide powder were analyzed by X-ray powder diffraction using Rigaku D/MAX 2500 at 50 kV/200 mA of nickel filtered copper Kα radiation. The samples were scanned from 5 to 50 degrees of 2θ in steps of 0.03 degrees at 2 degrees of 2θ per minute for the signal acquisition. Reflection geometry was used and samples were rotated at 20 RPM. Samples were dry powders press-packed and leveled into standard volume XRD sample holders.

Figure 1:
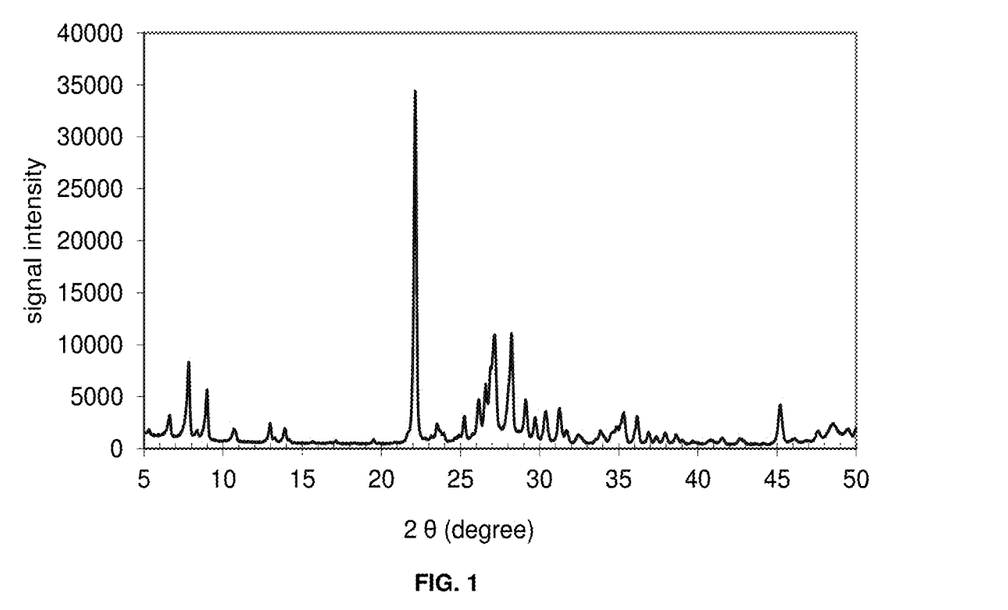
FIG. 1 shows the X-ray diffraction pattern of a MoVTeNb oxide finishing catalyst according to an embodiment of the present invention.

The X-ray diffraction pattern of the MoVTeNb oxide is illustrated in FIG. 1 which shows the orthorhombic phase as the major crystal phase with main peaks with 2θ at 6.7°, 7.8°, 22.1°, and 27.2°.

The MoVTeNb oxide was crushed into particles of <10 mesh after calcination. The particles were then ground in the "cryo-grinder", a model 6850 Freezer/Mill from SPEX CertiPrep (Metuchen, New Jersey, USA). About 5 grams of the small particles were placed in a cylindrical plastic tube along with a steel cylinder. The ends of the tube were capped with steel. The entire apparatus was immersed in liquid nitrogen, and then the steel cylinder was shuttled back and forth within the tube by the action of a magnet. The sample was pre-cooled for 5 min before 3.5 min grinding. After 2 min interval of cooling, the sample was ground again for another 3.5 min. The ground powder was removed from the tube and pressed/sieved into 14-20 mesh particles for performance evaluation in Example 1, below.

Synthesis 2 Preparation of Crystalline $Mo_3VO_x$ Catalyst

Crystalline $Mo_3VO_x$ catalyst was prepared according to the procedure reported in Catal. Sci. Technol., 2016, 6, 617-629 and the reference cited in the article. Similar hydrothermal synthesis procedure was used in the preparation of Mo—V based oxide catalyst as disclosed in WO 2005/120702 A1 and U.S. Pat. No. 9,181,169 B2.

Both the vanadyl sulfate (7.0 g $VOSO_4.nH_2O$) and ammonium heptamolybdate (14.5 g $(NH_4)_6Mo_7O_{24}$) were each dissolved in 200 ml high purity water. Once fully dissolved, the blue vanadate solution was poured into the colorless molybdate solution, producing a dark brown suspension.

After stirring 10 minutes, the pH was adjusted to 2.2 by dropwise addition of concentrated sulfuric acid. The mixture was stirred for 2 hours at ambient then divided into 5 of 125 ml Parr digestion reactors.

Each reactor was sealed and all placed into an oven at 175° C. After 18 hours at temperature of 175° C., the oven was turned off and allowed to cool to <100° C. The reactors were removed and cooled in water. When opened, the clear, slightly colored supernatant was poured off and the dark solids were scrapped out with fresh water and collected. All products were combined and washed on the filter with a large excess of fresh water.

The solids were dried at 90° C. The dried solids were crushed and then suspended for 30 minutes in 325 ml of 0.4 M oxalic acid (16.5 g oxalic acid/325 ml water). Then the extracted solids were collected by filtration and washing with an excess of water, then dried at 90° C.

About half of the dried powder was placed in a quartz boat and inserted into a quartz tube in a tube furnace. A purge of nitrogen was established for 10 minutes, then the system heated to 500° C. over several hours, held at temperature for 2 hours and allowed to slowly cool to ambient, all while maintaining the nitrogen purge. After collecting the thermally treated solids, a second batch was run with the remaining untreated sample.

Solids were combined into a single sample. The sample was pressed and sieved into 14-20 mesh particles, which was ready for performance evaluation.

The samples were run on a Bruker D8 diffractometer using Cu Kα radiation (wavelength 1.54059 Å). The samples were scanned from 5 to 50 degrees of 2θ. Reflection geometry was used and samples were rotated at 20 RPM. Samples were dry powders press-packed and leveled into standard volume XRD sample holders.

Figure 2:
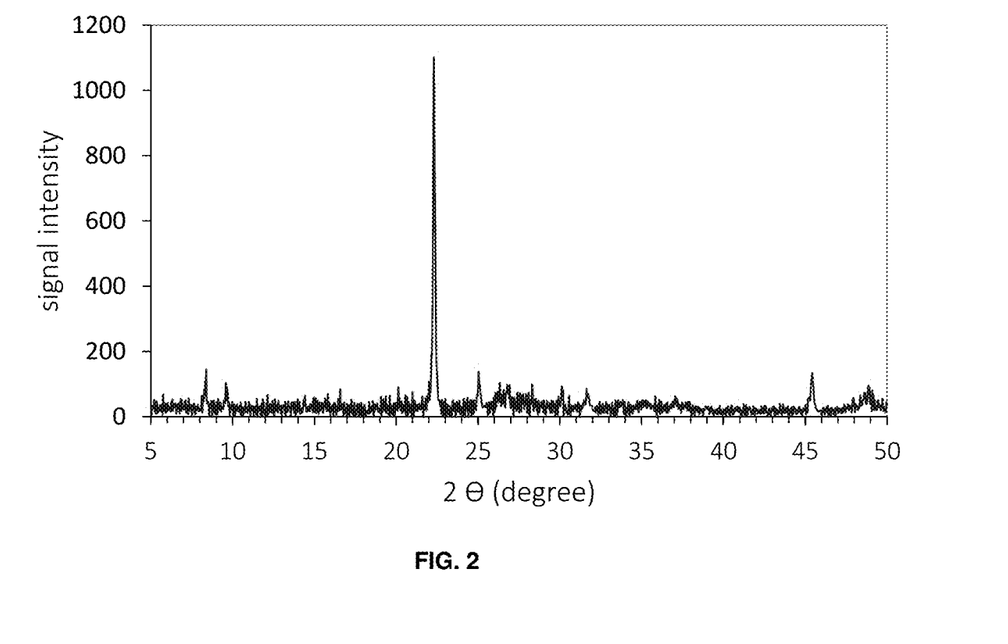
FIG. 2 shows the X-ray diffraction pattern of a $Mo_3VO_x$ catalyst.

The XRD pattern of the oxide with nominal composition $Mo_3VO_x$ oxide is shown in FIG. 2, which shows the oxide contains orthorhombic phase.

Comparative Example 1 Oxidation of the $1^{st}$ Stage Reactor Effluent from Propylene Oxidation to Acrolein Using Commercial R2 Catalyst Alone Propylene oxidation to acrolein and acrylic acid was conducted in two stages. Oxidation of propylene was conducted in a tubular reactor to generate a gaseous mixture similar to the first step in a two-step propylene oxidation process to produce acrylic acid. 15 ml of a Mo- and Bi-based mixed metal oxide catalyst R1 (propylene-oxidizing catalyst) from Nippon Kayaku Co. (Tokyo, Japan) was mixed with 15 ml of ⅛" Denstone™ 57 beads (Saint-Gobain Norpro, Stow, OH), before being loaded into a 2.54 cm (1") outer diameter (OD) stainless steel (SS) first stage tube reactor (0.834" ID). The reactor tube was heated to >340° C. in a clam-shell electrical furnace. The feed to the first stage tube reactor was a mixture of 24.0 ml/min propylene, 211.6 ml/min air, 34.0 ml/min N2, and 1.44 gram/h deionized water. The values of all gas flow rates were under standard temperature (0° C.) and standard pressure (101.3 kPa) conditions. The water was injected by a syringe pump into a SS mixer vessel heated to 160-170° C. The other feed gases were controlled by mass flow controller. The effluent from the first stage reactor, designated as R1-Exit, was fed directly to the $2^{nd}$ stage reactor via an externally heated transfer line with skin temperature controlled at 170-200° C.

The temperature of the 1 st stage reactor was adjusted to obtain propylene conversion consistently in the range of 96.0-97.5%, and oxygen conversion in the range of 66-69%. The conversions of propylene and oxygen were calculated using the formula below.

Propylene conversion (%)=(moles of propylene fed−moles of propylene in R1-Exit)/moles of propylene fed.

Oxygen conversion (%)=(moles of oxygen fed−moles of oxygen in R1-Exit)/moles of oxygen fed.

R1-Exit was used as feed to evaluate the performance of the $2^{nd}$ stage reactor in oxidizing acrolein and acetaldehyde to corresponding acids. A typical composition of R1-Exit was listed in Table 1 with propylene conversion at 96.5% and $O_2$ conversion at 67.7%.

TABLE 1

Typical concentration of main components in R1-Exit

| Component | Mole % |
|---|---|
| $CO_2$ | 0.51 |
| $C_3H_6$ | 0.26 |
| $O_2$ | 4.31 |
| Argon | 0.62 |
| $N_2$ | 60.2 |
| CO | 0.29 |
| $H_2O$ | 26.8 |
| Acetaldehyde | 0.15 |
| Acrolein | 5.94 |
| Acetic acid | 0.041 |
| Acrylic acid | 0.85 |

15 ml of a Mo- and V-based commercial R2 catalyst (acrolein-oxidizing catalyst) from Nippon Kayaku Co. (Tokyo, Japan) was mixed with 15 ml of ⅛" Denstone™ beads. The mixture was loaded into the feed inlet side of a U-shaped SS tube with 1" OD and 0.834" ID. The other internal space of the U-shaped tube was filled with Denstone™ beads. The U-shaped tube was put into a fluidized sand bath furnace with the catalyst bed section immersed in the sand bath. The air was used to fluidize the sand at flow rate of 3.3-3.5 SCFM (standard cubic feet per minute). The temperature difference in the bath was controlled no more than 3° C. by maintaining high air flow rate. The bath temperature was raised to achieve higher conversion of acrolein to acrylic acid along with oxidation of other organic components such as acetaldehyde in R1-Exit. The effluent from the $2^{nd}$ stage reactor was designated as R2-Exit.

The R1-Exit or R2-Exit was collected independently and analyzed. The effluent first flew through Trap 1 which was a 100-500 ml stainless vessel wrapped with ¼" copper coil connected to a recirculation chiller set at 0-1° C. The gases escaping the Trap 1 flew through a second trap, Trap 2, immersed in water/ice, and third and fourth traps (Trap 3A and Trap 3B) immersed in dry ice/iso-propanol mixture. Trap 2 served mainly as a protection trap to prevent high amount of water or acrylic acid getting into a dry ice/iso-propanol trap because water/AA could freeze in dry ice/iso-propanol trap and cause pressure buildup. The trap collection time was typically 2-4 hours. An inhibitor solution of 6-12 grams was injected to Trap 2, Trap 3A and 3B before sample collection to prevent polymer formation. Trap 2 collected very little material most times. 0.2 wt. % of hydroquinone in iso-propanol was used as inhibitor solution.

The off gas from the dry ice/iso-propanol trap was analyzed on-line by a GC equipped with Thermal Conductivity Detector and 5 Å mol-sieve/silica gel column. The main gas components in the off gas typically included nitrogen, oxygen, unreacted propylene, carbon monoxide, and carbon dioxide. The liquids collected from Trap 1 and Trap 2 (if any) were combined into one sample, labeled as T-1 sample. The liquid collected from Trap 3A and Trap 3B were labeled as T-3A and T-3B sample, respectively. The T-1, T-3A and T-3B samples were sent to off-line analysis by a GC equipped with Flame Ionization Detector and a capillary column (DB-FFAP 123-3232E). The amounts of major products such as acrylic acid, acrolein, acetaldehyde, acetone, propionic acid, acetic acid were obtained.

The yields of acrolein, acetaldehyde, and acrylic acid, and carbon mass balance after the $2^{nd}$ stage reactor were calculated using the formula below:

Yield of acrolein (%)=(moles of acrolein in R2-Exit)/moles of propylene fed*100

Yield of acetaldehyde (%)=(moles of acetaldehyde in R2-Exit/1.5)/moles of propylene fed*100

Yield of acrylic acid (%)=(moles of acrylic acid in R2-Exit)/moles of propylene fed*100

Carbon mass balance (%)=(total amount of carbon from molecules in R2-Exit including CO2, CO, propylene, formaldehyde,acetaldehyde,acrolein, acetic acid, propionic acid, acrylic acid)/(total amount of carbon from propylene fed)*100

The acrolein yield, acetaldehyde yield, and acrylic acid yield are listed in Table 2, below. The yields of acrolein and acetaldehyde were reduced along with increasing R2 reactor bath temperature, and the AA yield increased accordingly. However, even at 292° C., the acrolein yield was still 1.91% with acetaldehyde yield at 0.074%, and the AA yield was up to 86%.

Figure 3:
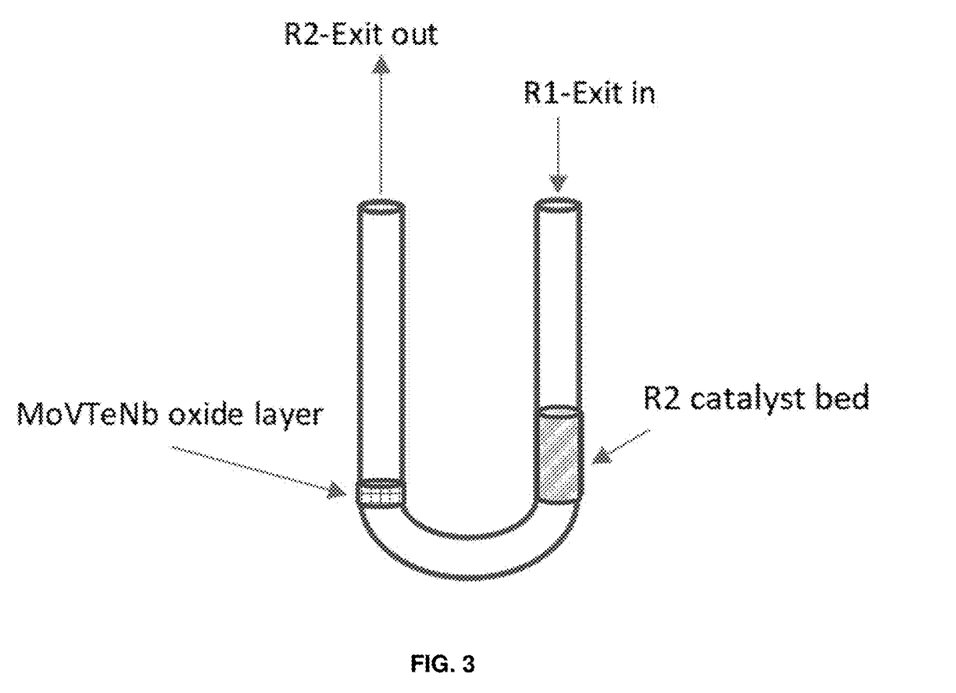
FIG. 3 shows the packing of an acrolein-oxidizing catalyst and a finishing catalyst in a reactor tube in accordance with an embodiment of the present invention.

Example 1 Addition of MoVTeNb Oxide Finishing Catalyst after Commercial R2 Catalyst Bed in the Oxidation of the $1^{st}$ Stage Reactor Effluent from Propylene Oxidation to Acrolein The test condition remained the same as in "Comparative Example 1" except a mixture of 1.0 gram of 14-20 mesh of MoVTeNb oxide particles (prepared in Synthesis 1) and 9.0 grams of Carborundum #12 granules (from Hengar Co., Thorofare, NJ) as diluent was loaded in the outlet arm of the "U-shaped" reactor tube as illustrated in FIG. 3. The space above and below the catalyst bed was filled with Denstone™ 57 beads.

The yields of acrolein, acetaldehyde, and acrylic acid were listed in Table 2. The acrolein yield dropped to 1.2% at bath temperature of 277° C., and the acetaldehyde was below the detection limit (~5 ppm in the liquid sample). The acrolein yield dropped below 1% at bath temperature of 282° C., and the AA yield was at 87%.

Comparative Example 2 Addition of $Mo_3VO_x$ Oxide Catalyst after Commercial R2 Catalyst Bed in the Oxidation of the $1^{st}$ Stage Reactor Effluent from Propylene Oxidation to Acrolein The test conditions remained the same as in Example 1 except the MoVTeNb oxide layer was replaced by a mixture of 1.0 gram of 14-20 mesh $Mo_3VO_x$ oxide particles (prepared in Synthesis 2) and 9.0 grams of Carborundum #12 granules as diluent.

The yield of acrolein, acetaldehyde, and acrylic acid were listed in Table 2. The acrolein yield was reduced to 1.05% at R2 bath temperature of 287° C., however, acetaldehyde yield was at 0.112%, and the AA yield was only 85.2

TABLE 2

Comparison of product yields at different bath temperature of 2$^{nd}$ stage reactor

| Examples | R2 Bath T (° C.) | C3H6 Conv. (%) | Yield (%) Acetaldehyde | Acrolein | AA* | Carbon Mass Balance (%) |
|---|---|---|---|---|---|---|
| Comparative Example 1 | 267 | 96.7 | 0.546 | 24.9 | 62.0 | 99.5 |
|  | 277 | 97.0 | 0.245 | 7.37 | 80.4 | 99.4 |
|  | 283 | 97.2 | 0.130 | 3.59 | 84.0 | 99.5 |
|  | 292 | 97.3 | 0.074 | 1.91 | 86.0 | 99.4 |
| Example 1 | 267 | 97.0 | 0.176 | 3.38 | 85.0 | 99.5 |
|  | 277 | 97.3 | <0.005 | 1.20 | 87.0 | 99.5 |
|  | 282 | 97.3 | <0.005 | 0.90 | 87.0 | 99.5 |
| Comparative Example 2 | 282 | 96.8 | 0.110 | 1.23 | 83.7 | 99.5 |
|  | 287 | 98.0 | 0.112 | 1.05 | 85.2 | 99.5 |

*AA yield was adjusted to obtain carbon mass balance close to 99.5%.

It is surprising to find that the additional small amount of MoVTeNb oxide finishing catalyst with orthorhombic crystal phase can significantly reduce the bath temperature required to reduce acrolein yield while increasing AA yield compared to using the commercial R2 catalyst alone. Lower bath temperature can slow down the deactivation of the commercial R2 catalyst. Furthermore, the reduction of acetaldehyde below detection limit (~5 ppm in the liquid sample) can alleviate the fouling in the downstream separation caused by acetaldehyde.

The use of additional $Mo_3VO_x$ oxide (Comparative Example 2) reduced the bath temperature required to achieve lower acrolein yield compared to using commercial R2 catalyst alone. However, the yield of acetaldehyde was not preferably reduced and the AA yield was slightly lower compared to using commercial R2 catalyst alone.

We claim:

1. A process for producing acrylic acid comprising:
   a) contacting a gas stream comprising acrolein with an acrolein-oxidizing catalyst to form a product stream A, wherein at least one aldehyde byproduct is present in the product stream A;
   b) contacting the product stream A with a finishing catalyst to form a product stream B comprising acrylic acid, wherein the product stream B comprises a lower weight percentage of the at least one aldehyde byproduct than product stream A;
   wherein:
   i) the acrolein-oxidizing catalyst comprises a mixed metal oxide catalyst of general formula (I):

$$MoV_aA^1{}_bA^2{}_cA^3{}_dO_m \quad (I)$$

wherein:
   $A^1$ comprises at least one element selected from the group consisting of W and Cu;
   $A^2$ comprises at least one element selected from the group consisting of Sb, Fe, and Nb;
   $A^3$ comprises at least one element selected from the group consisting of Y, Ti, Zr, Hf, Ta, Cr, Mn, Re, Ru, Co, Rh, Ir, Ni, Pd, Pt, Ag, Au, Zn, B, Al, Ga, In, Ge, Sn, Si, Te, Pb, P, As, Bi, Se, rare earth elements, alkaline elements, and alkaline earth elements;
   a ranges from 0.01 to 1.0;
   b ranges from 0.01 to 1.5;
   c ranges from 0 to 1.5;
   d ranges from 0 to 1.0; and
   m is dependent on the oxidation state of the other elements;
   ii) the finishing catalyst comprising a mixed metal oxide catalyst of general formula (II):

$$MoV_wNb_xX^1{}_yX^2{}_zO_n \quad (II)$$

wherein:
   $X^1$ comprises at least one element selected from the group consisting of Te and Sb;
   $X^2$ comprises at least one an element selected from the group consisting of Y, Ti, Zr, Hf, Ta, Cr, Mn, Re, Fe, Ru, Co, Rh, Ir, Ni, Pd, Pt, Ag, Au, Zn, B, Al, Ga, In, Ge, Sn, Pb, P, As, Bi, Se, rare earth elements and alkaline earth elements;
   w ranges from 0.01 to 1.0;
   x ranges from 0.01 to 1.0;
   y ranges from 0.01 to 1.0;
   z ranges from 0.001 to 1.0;
   n is depended on the oxidation state of the other elements;
   the finishing catalyst does not contain W or Cu, and has an X-ray diffraction pattern showing an orthorhombic phase as the major crystal phase with main peaks with 2θ at 6.7°, 7.8°, 22.1°, and 27.2°; and
   the acrolein-oxidizing catalyst has a different chemical composition than the finishing catalyst.

2. The process according to claim 1, wherein the acrolein-oxidizing catalyst is positioned upstream from the finishing catalyst.

3. The process according to claim 1, wherein the acrolein-oxidizing catalyst and the finishing catalyst are formed as a single catalyst bed in a reactor.

4. The process according to claim 1, wherein the finishing catalyst is present in reactor following a reactor containing the acrolein-oxidizing catalyst.

5. The process according to claim 1, further comprising:
   prior to step a), preparing the gas stream comprising acrolein by oxidizing propylene in the presence of a propylene-oxidizing catalyst.

6. The process according to claim 1, wherein the finishing catalyst comprises less than 20 wt. % based on the total weight of the acrolein-oxidizing catalyst and the finishing catalyst.

* * * * *